US00PP18073P2

(12) United States Plant Patent
Theobald

(10) Patent No.: US PP18,073 P2
(45) Date of Patent: Sep. 25, 2007

(54) ***VERONICA* PLANT NAMED 'VEROBIBLUE'**

(50) Latin Name: *Veronica peduncularis*
Varietal Denomination: Verobiblue

(75) Inventor: Hendrik Theobald, Heidesheim (DE)

(73) Assignee: InnovaPlant GmbH + Co. KG, Gensingen (DE)

( * ) Notice: Subject to any disclaimer, the term of this patent is extended or adjusted under 35 U.S.C. 154(b) by 0 days.

(21) Appl. No.: 11/299,956

(22) Filed: Dec. 12, 2005

(51) Int. Cl.
*A01H 5/00* (2006.01)

(52) U.S. Cl. ..... Plt./251
(58) Field of Classification Search ..... Plt./251
See application file for complete search history.

(56) References Cited

PUBLICATIONS

UPOV–ROM GTITM, Plant Variety Database, 2006/03, GTI Jouve Retrieval Software, citation for *veronica* 'Verobiblue' for Canada (CA) and The European Community (QZ).*

* cited by examiner

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Veronica* plant named 'Verobiblue', characterized by its upright, uniform, outwardly spreading and low-mounding plant habit; freely basal branching habit, dense and bushy plant form; early, freely and long flowering habit; and deep violet blue-colored flowers.

2 Drawing Sheets

Botanical designation: *Veronica peduncularis.*
Cultivar denomination: 'Verobiblue'.

BACKGROUND OF THE INVENTION

The present Invention relates to a new and distinct cultivar of *Veronica* plant, botanically known as *Veronica peduncularis,* and hereinafter referred to by the cultivar name 'Verobiblue'.

The new *Veronica* is a naturally-occurring whole plant mutation of the *Veronica peduncularis* cultivar Georgia Blue, not patented. The new *Veronica* was discovered and selected by the Inventor in 2002 from within a population of plants of the cultivar Georgia Blue in a controlled environment in Gensingen, Germany.

Asexual reproduction of the new cultivar by cuttings since the Spring of 2002 in Gensingen, Germany, has shown that the unique features of this new *Veronica* are stable and reproduced true to type in successive generations.

SUMMARY OF THE INVENTION

Plants of the cultivar 'Verobiblue' have not been observed under all possible environmental conditions. The phenotype may vary somewhat with variations in environment such as temperature and light intensity without, however, any variance in genotype.

The following traits have been repeatedly observed and are determined to be the unique characteristics of 'Verobiblue'. These characteristics in combination distinguish 'Verobiblue' as a new and distinct *Veronica* cultivar:

1. Upright, uniform, outwardly spreading and low-mounding plant habit.
2. Freely basal branching habit, dense and bushy plant form.
3. Early, freely and long flowering habit.
4. Bright violet blue-colored flowers.

Plants of the new *Veronica* can be compared to the parent, the cultivar Georgia Blue. Plants of the new *Veronica* differ from plants of the cultivar Georgia Blue in the following characteristics:

1. Plants of the new *Veronica* flower earlier than plants of the cultivar Georgia Blue.
2. Plants of the new *Veronica* have larger flowers than plants of the cultivar Georgia Blue.
3. Plants of the new *Veronica* have darker blue-colored flowers than plants of the cultivar Georgia Blue.

Plants of the new *Veronica* can also be compared to plants of the *Veronica peduncularis* cultivar Alba, not patented. Plants of the new *Veronica* differ from plants of the cultivar Alba in the following characteristics:

1. Plants of the new *Veronica* flower earlier than plants of the cultivar Alba.
2. Plants of the new *Veronica* have larger flowers than plants of the cultivar Alba.
3. Plants of the new *Veronica* and the cultivar Alba differ in flower color as plants of the cultivar Alba have white-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Veronica.*

The photograph on the first sheet comprises a side perspective view of a typical plant of 'Verobiblue' grown in an outdoor nursery.

The photograph on the second sheet is a close-up view of typical flowers of 'Verobiblue'.

DETAILED BOTANICAL DESCRIPTION

Plants shown in the aforementioned photographs and used in the following description were grown under conditions which closely approximate commercial production conditions during the summer in an outdoor nursery in Bonsall, Calif. During the production of the plants, day temperatures ranged from 15° C. to 28° C. and night temperatures ranged from 5° C. to 15° C. Plants were about two months old when the photographs and description were taken. In the following description, color references are made to The Royal Horticultural Society Colour Chart, 1995 Edition, except where general terms of ordinary dictionary significance are used.

Botanical classification: *Veronica peduncularis* cultivar 'Verobiblue'.

Parentage: Naturally-occurring whole plant mutation of the *Veronica peduncularis* cultivar Georgia Blue, not patented.

Propagation:

*Type.*—By cuttings.

*Time to initiate roots.*—Summer: About 14 days at 20° C. Winter: About 18 days at 20° C.

*Time to produce a rooted cutting.*—About 20 days at 20° C.

*Root description.*—Fine; white in color.

*Rooting habit.*—Freely branching.

Plant description:

*Form.*—Upright, uniform and outwardly spreading plant habit; low-mounding. Freely basal branching; dense and bushy plant habit; moderately vigorous growth habit. Numerous flowers arranged on terminal and axillary racemes.

*Plant height.*—About 9 cm.

*Plant width.*—About 39 cm.

*Lateral stem description.*—Length (excluding inflorescence): About 16 cm. Diameter: About 1.5 mm. Internode length: About 2 cm. Strength: Moderately strong to strong; flexible. Texture: Pubescent. Color, vegetative stems: Close to 146A. Color, flowering stems: Close to 187A.

*Foliage description.*—Arrangement: Opposite, simple. Length: About 2 cm. Width: About 1.5 cm. Shape: Ovate. Apex: Acute. Base: Obtuse. Margin: Serrate. Texture, upper and lower surfaces: Slightly pubescent. Venation pattern: Pinnate; arcuate. Color: Developing and fully expanded foliage, upper surface: 147A. Developing and fully expanded foliage, lower surface: 147B. Venation, upper and lower surfaces: Similar to lamina.

Flower description:

*Flower arrangement and shape.*—Single rotate flowers arranged on terminal and axillary racemes; flowers face mostly outward and upright. Freely flowering habit, about 25 flowers per raceme.

*Natural flowering season.*—Early and continuous flowering from May to early July in Germany.

*Flower longevity on the plant.*—Individual flowers last about one to two weeks on the plant. Flowers not persistent.

*Fragrance.*—None detected.

*Flower buds.*—Length: About 3 mm. Diameter: About 2 mm. Shape: Ovate. Color: Close to 83A.

*Flowers.*—Diameter: About 1 cm. Depth (height): About 1 cm.

*Petals.*—Arrangement: Rotate; four petals in a single whorl fused at the base. Length: About 5 mm. Width: About 6 mm. Shape: Roughly obovate. Apex: Mostly rounded. Margin: Entire. Texture, upper and lower surfaces: Smooth, glabrous; satiny. Color: When opening, upper surface: Close to 99C. When opening, lower surface: Close to 99D. Fully opened, upper surface: Close to 96A; color becoming closer to 96B to 96C to 96D with development. Fully opened, lower surface: Close to 96B to 96D. Center of flower: Close to 155D.

*Sepals.*—Arrangement: Four sepals in a single whorl. Length: About 3 mm. Width: About 1.5 mm. Shape: Lanceolate. Apex: Acute. Base: Fused. Margin: Entire. Texture, upper and lower surfaces: Smooth, glabrous. Color, upper and lower surfaces: Close to 146A.

*Pedicels.*—Length: About 7 mm. Diameter: Less than 1 mm. Strength: Strong; flexible. Color: Close to 187A.

*Reproductive organs.*—Stamens: Quantity per flower: Two. Anther shape: Oblanceolate. Anther length: Less than 1 mm. Anther color: Close to 155D. Pollen amount: None observed. Pistils: Quantity per flower: One. Pistil length: About 4 mm. Stigma shape: Rounded. Stigma color: Close to 155D. Style length: About 3 mm. Style color: Close to 155D. Ovary color: Close to 146A. Seed: Seed development has not been observed.

Disease/pest resistance: Plants of the new *Veronica* have not been noted to be resistant to pathogens and pests common to *Veronica*.

Temperature tolerance: Plants of the new *Veronica* have been observed to tolerate temperatures from −8° C. to 25° C.

It is claimed:

1. A new and distinct cultivar of *Veronica* plant named 'Verobiblue', as illustrated and described.

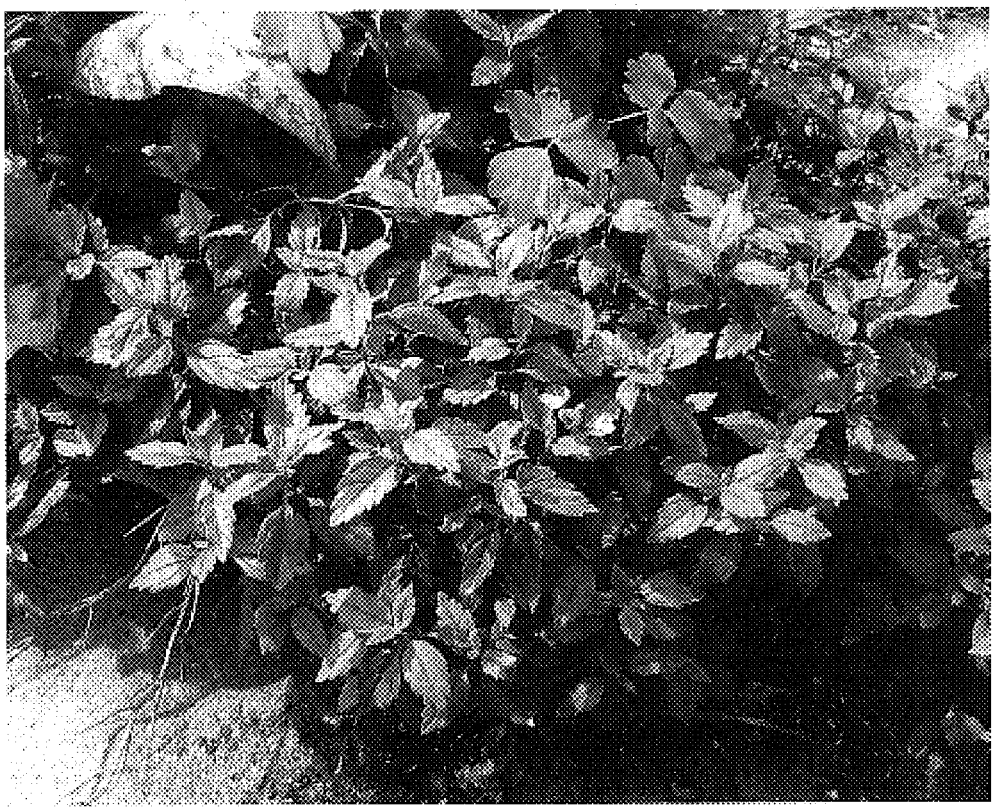

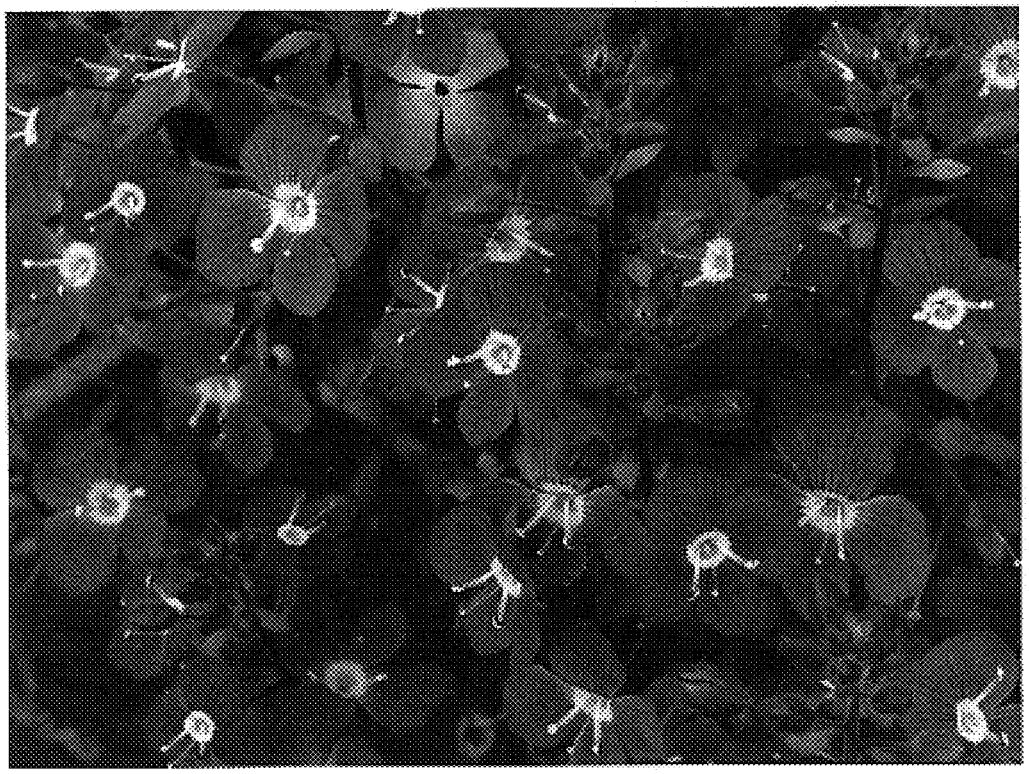

* * * * *